US006268382B1

(12) United States Patent
Woosley et al.

(10) Patent No.: US 6,268,382 B1
(45) Date of Patent: Jul. 31, 2001

(54) METHODS AND COMPOSITIONS FOR TREATING ALLERGIC DISORDERS AND OTHER DISORDERS USING NORASTEMIZOLE IN COMBINATION WITH OTHER ACTIVE INGREDIENTS

(75) Inventors: Raymond L. Woosley, Washington, DC (US); A. K. Gunnar Aberg, Westborough, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/650,645

(22) Filed: Aug. 30, 2000

Related U.S. Application Data

(60) Continuation of application No. 09/551,613, filed on Apr. 17, 2000, now Pat. No. 6,187,795, which is a division of application No. 09/481,439, filed on Jan. 12, 2000, now Pat. No. 6,187,794, which is a division of application No. 08/766,094, filed on Dec. 16, 1996, now Pat. No. 6,124,320, which is a continuation of application No. 08/182,685, filed on Jan. 18, 1994, now Pat. No. 6,130,233, which is a continuation of application No. 07/940,054, filed on Sep. 3, 1992, now abandoned.

(51) Int. Cl.[7] ................................................. A61K 31/445

(52) U.S. Cl. ............................................................. 514/322
(58) Field of Search .............................................. 514/322

Primary Examiner—Samuel Barts
(74) Attorney, Agent, or Firm—Pennie & Edmonds LLP

(57) ABSTRACT

Methods and compositions are disclosed utilizing metabolic derivatives of astemizole for the treatment of allergic disorders while avoiding the concomitant liability of adverse effects associated with the astemizole. The metabolic derivatives of astemizole are also useful for the treatment of retinopathy and other small vessel disorders associated with diabetes mellitus and such other conditions as may be related to the antihistamine activity of astemizole. For example, the metabolic derivatives of astemizole are useful for the treatment of asthma, motion sickness, and vertigo, without the concomitant liability of adverse effects associated with astemizole. Furthermore, the metabolic derivatives of astemizole, in combination with non-steroidal anti-inflammatory agents or other non-narcotic analgesics, or in combination with a decongestant, cough suppressant/antitussive or expectorant, are useful for the treatment of cough, cold, cold-like, and/or flu symptoms and the discomfort, headache, pain, fever, and general malaise associated therewith, without the concomitant liability of adverse effects associated with astemizole.

8 Claims, No Drawings

METHODS AND COMPOSITIONS FOR TREATING ALLERGIC DISORDERS AND OTHER DISORDERS USING NORASTEMIZOLE IN COMBINATION WITH OTHER ACTIVE INGREDIENTS

This is a continuation of application Ser. No. 09/551,613, filed Apr. 17, 2000, now U.S. Pat. No. 6,187,795, which is a divisional of application Ser. No. 09/481,439, filed Jan. 12, 2000, now U.S. Pat. No. 6,187,794, which is a divisional of application Ser. No. 08/766,094, filed Dec. 16, 1996, now U.S. Pat. No. 6,124,320, which is a continuation of application Ser. No. 08/182,685, filed Jan. 18, 1994, now U.S. Pat. No. 6,130,233, which is a continuation of application Ser. No. 07/940,054, filed Sep. 3, 1992, now abandoned.

1. BACKGROUND OF THE INVENTION

This invention relates to novel pharmaceutical compositions containing desmethylastemizole, 6-hydroxydesmethylastemizole and norastemizole. These compositions possess potent antihistaminic activity and are useful in treating allergic rhinitis, asthma and other allergic disorders while avoiding adverse effects associated is with the administration of other antihistamines, such as astemizole, including but not limited to cardiac arrhythmias, drowsiness, nausea, fatigue, weakness and headache. Also, these compositions, in combination with non-steroidal anti-inflammatory agents or other non-narcotic analgesics, are useful for the treatment of cough, cold, cold-like, and/or flu symptoms and the discomfort, headache, pain, fever, and general malaise associated therewith. The aforementioned combinations may optionally include one or more other active components including a decongestant, cough suppressant/antitussive, or expectorant.

Additionally, these novel pharmaceutical compositions containing desmethylastemizole, 6-hydroxydesmethylastemizole and norastemizole are useful in treating motion sickness, vertigo, diabetic retinopathy, small vessel complications due to diabetes and such other conditions as may be related to the activity of these derivatives as antagonists of the H-1 histamine receptor while avoiding the adverse effects associated with the administration of other antihistamines, such as astemizole.

Also disclosed are methods for treating the above-described conditions in a human while avoiding the adverse effects that are associated with the administration of other antihistamines, such as astemizole, by administering the aforementioned pharmaceutical compositions containing desmethylastemizole, 6-hydroxydesmethylastemizole and norastemizole to said human.

The active compounds of these compositions and methods are metabolic derivatives of astemizole. Chemically, these derivatives are desmethylastemizole, 6-hydroxydesmethylastemizole and norastemizole. These compounds are described in Kamei et al., *Arzneimittel-Forschung/Drug Research*, 41: 932–36 (1991).

Astemizole is an antagonist of the H-1 histamine receptor protein. Histamine receptor proteins occur in two well-identified forms in tissues, of which H-1 and H-2 receptors are two. The H-1 receptors are those that mediate the response antagonized by conventional antihistamines. H-1 receptors are present, for example, in the ileum, the skin, and the bronchial smooth muscle of man and other mammals. Astemizole antagonizes the effect of histamine in the guinea pig isolated ileum, suppresses histamine-induced whealing in the skin of guinea pigs, and protects against histamine induced bronchoconstriction in the guinea pig.

Through H-2 receptor-mediated responses, histamine stimulates gastric acid secretion in mammals and the chronotropic effect in isolated mammalian atria. Astemizole has no effect on histamine-induced gastric acid secretion, nor does it alter the chronotropic effect of histamine on atria. Thus, astemizole has no apparent effect on the H-2 histamine receptor.

Astemizole is well absorbed but is extensively metabolized. See Uchiyama et al., *Pharmacometrics*, 40: 77–93 (1990). Three main metabolites have been identified, and all of the metabolites are reported to have antihistaminic activity. See Kamei et al., *Arzneimittel-Forschung/Drug Research*, 41: 932–36 (1991).

On the basis of its antihistaminic activity, researchers evaluated the pharmacological effects of astemizole in man. Clinical trials of efficacy indicated that astemizole is an effective H-1 antagonist. See Howarth, *Clin. Exp. Allergy*, 20 (Suppl. 2): 31–41 (1990).

Weintraub et al., *Hosp. Formul.*, 22: 918–27 (1987) describes clinical efficacy of astemizole in the treatment of both seasonal and perennial allergies. It has also been suggested that astemizole would be useful for the treatment of asthma.

Astemizole may also be useful for the treatment of motion sickness and vertigo. Some antihistamines have been found to be effective for the prophylaxis and treatment of motion sickness. See Wood, *Drugs*, 17: 471–479 (1979). Some antihistamines have also proven useful for treating vestibular disturbances, such as Meniere's disease, and in other types of vertigo. See Cohen et al., *Archives of Neurology*, 27: 129–135 (1972).

In addition, astemizole may be useful in the treatment of diabetic retinopathy and other small vessel disorders associated with diabetes mellitus. In tests on rats with streptozocin-induced diabetes, treatment by antihistamines prevented the activation of retinal histamine receptors which have been implicated in the development of diabetic retinopathy. The use of antihistamines to treat retinopathy and small vessel disorders associated with diabetes mellitus is disclosed in U.S. Pat. No. 5,019,591.

It has also been suggested that astemizole, in combination with non-steroidal anti-inflammatory agents or other non-narcotic analgesics, would be useful for the treatment of cough, cold, cold-like and/or flu symptoms and the discomfort, pain, headache, fever, and general malaise associated therewith. These compositions for the treatment of the above-described symptoms may optionally include one or more other active components including a decongestant (such as pseudoephedrine), a cough suppressant/antitussive (such as dextromethorphan) or an expectorant (such as guaifenesin).

Many antihistamines cause somewhat similar adverse effects. These adverse effects include but are not limited to sedation, gastrointestinal distress, dry mouth, and constipation or diarrhea. Astemizole has been found to cause relatively less sedation as compared with other antihistamines. See Weintraub et al., *Hosp. Formul.*, 22: 918–27 (1987).

However, the administration of astemizole to a human has been found to cause other adverse effects. These adverse effects include but are not limited to cardiac arrhythmias, including ventricular tachyarrhythmias, torsades de pointes, and ventricular fibrillation. See Knowles, *Canadian Journal Hosp. Pharm.*, 45: 33,37 (1992); Craft, *British Medical Journal*, 292: 660 (1986); Simons et al., *Lancet*, 2: 624 (1988); and Unknown, *Side Effects of Drugs Annual*, 12: 142 and 14: 135. An additional unwanted side effect of astemizole is appetite stimulation and weight gain in patients taking the drug for various indications. See Krstenansky et al., *Drug Intell. Clin. Pharm.*, 21: 947–53 (1987).

Thus, it would be particularly desirable to find a compound with the advantages of astemizole which would not have the aforementioned disadvantages.

2. SUMMARY OF THE INVENTION

It has now been discovered that desmethylastemizole, 6-hydroxydesmethylastemizole and norastemizole (hereinafter metabolic derivatives of astemizole) are effective antihistamines which avoid adverse effects which are associated with the administration of astemizole, including but not limited to cardiac arrhythmias, cardiac conduction disturbances, appetite stimulation, weight gain, sedation, gastrointestinal distress, dry mouth, and constipation or diarrhea. It has also been discovered that these pharmaceutical compositions containing metabolic derivatives of astemizole are useful in treating allergic disorders and such other conditions as may be related to the composition's activity as an antihistamine, including but not limited to allergic rhinitis, solar urticaria, and symptomatic dermographism, while avoiding the above-described adverse effects associated with the administration of astemizole. The present invention also includes methods for treating the above-described conditions in a human while avoiding the adverse effects that are associated with astemizole, by administering the metabolic derivatives to said human.

Furthermore, it has now also been discovered that the metabolic derivatives of astemizole are useful in treating asthma while avoiding the adverse effects associated with administration of astemizole. As stated above, examples of such side effects are appetite stimulation, weight gain, cardiac arrhythmias and cardiac conduction disturbances. Also, these metabolic derivatives are useful for the treatment of motion sickness and vertigo, while avoiding the adverse effects associated with administration of astemizole. In addition, the metabolic derivatives of astemizole are useful in treating such disorders as retinopathy and small vessel disorders associated with diabetes mellitus while avoiding the adverse effects associated with administration of astemizole.

It has also been discovered that the metabolic derivatives of astemizole, in combination with non-steroidal anti-inflammatory agents or other non-narcotic analgesics, are useful for the treatment of cough, cold, cold-like and/or flu symptoms and the discomfort, pain, headache, fever, and general malaise associated therewith. The use of pharmaceutical compositions of the invention, containing the metabolic derivatives of astemizole, and non-narcotic analgesics or non-steroidal anti-inflammatory agents such as aspirin, acetaminophen or ibuprofen, may optionally include one or more other active components including a decongestant (such as pseudoephedrine), a cough suppressant/antitussive (such as dextromethorphan) or an expectorant (such as guaifenesin).

3. DETAILED DESCRIPTION OF THE INVENTION

The present invention encompasses a method of treating a human afflicted by or susceptible to an allergic disorder while avoiding the concomitant liability of adverse effects associated with the administration of astemizole, which comprises administering to said human afflicted by or susceptible to an allergic disorder an amount of one or more compounds selected from a class of metabolic derivatives of astemizole, or a pharmaceutically acceptable salt thereof, said amount being sufficient to treat said allergic disorder, but insufficient to cause the adverse effects associated with astemizole. Suitable metabolic derivatives are compounds selected from the group consisting of desmethylastemizole, 6-hydroxydesmethylastemizole and norastemizole, and the like.

The present invention also encompasses a composition adapted for the treatment of a human having an allergic disorder which comprises an amount of a metabolic derivative of astemizole, or a pharmaceutically acceptable salt thereof, said amount being sufficient to alleviate said allergic disorder but insufficient to cause the adverse effects associated with astemizole.

The present invention further encompasses a method of treating asthma in a human, while avoiding the concomitant liability of adverse effects associated with the administration of astemizole, which comprises administering to said human afflicted by asthma an amount of a metabolic derivative of astemizole or a pharmaceutically acceptable salt thereof, said amount being sufficient to alleviate said asthma but insufficient to cause the adverse effects associated with astemizole. Suitable metabolic derivatives of astemizole are compounds selected from the group consisting of desmethylastemizole, 6-hydroxydesmethylastemizole and norastemizole, and the like.

In addition, the present invention encompasses compositions adapted for the treatment of a human having asthma which comprises an amount of a metabolic derivative of astemizole, or a pharmaceutically acceptable salt thereof, said amount being sufficient to alleviate said asthma but insufficient to cause the adverse effects associated with astemizole.

A further aspect of the present invention includes a method of treating motion sickness or vertigo in a human, while avoiding the concomitant liability of adverse effects associated with the administration of astemizole, which comprises administering to said human afflicted by motion sickness or vertigo an amount of a metabolic derivative of astemizole, or a pharmaceutically acceptable salt thereof, said amount being sufficient to alleviate said motion sickness or vertigo but insufficient to cause the adverse effects associated with astemizole. Suitable metabolic derivatives of astemizole are compounds selected from the group consisting of desmethylastemizole, 6-hydroxydesmethylastemizole and norastemizole, and the like.

Furthermore, the present invention includes compositions for treating motion sickness or vertigo in a human which comprises an amount of a metabolic derivative of astemizole, or a pharmaceutically acceptable salt thereof, said amount being sufficient to alleviate said motion sickness or vertigo but insufficient to cause the adverse effects associated with astemizole.

Also included in the present invention is a method of treating retinopathy or other small vessel diseases associated with diabetes mellitus while avoiding the concomitant liability of adverse effects associated with the administration of astemizole, which comprises administering to said human an amount of a metabolic derivative of astemizole, or a pharmaceutically acceptable salt thereof, said amount being sufficient to alleviate said retinopathy or other small vessel diseases associated with diabetes mellitus but insufficient to cause the adverse effects associated with astemizole. Suitable metabolic derivatives of astemizole are compounds selected from the group consisting of desmethylastemizole, 6-hydroxydesmethylastemizole and norastemizole, and the like.

Additionally, the present invention includes compositions for treating retinopathy or other small vessel diseases associated with diabetes mellitus in a human, comprising an amount of a metabolic derivative of astemizole, or a pharmaceutically acceptable salt thereof, said amount being sufficient to alleviate said retinopathy or other small vessel diseases associated with diabetes mellitus but insufficient to cause the adverse effects associated with astemizole.

Furthermore, the present invention includes a pharmaceutical composition for use in the treatment of cough, cold, cold-like and/or flu symptoms and the discomfort, pain, fever and general malaise associated therewith, in a human, said composition comprising (i) a therapeutically effective amount of at least one metabolic derivative of astemizole, with (ii) a therapeutically effective amount of at least one non-steroidal anti-inflammatory agent or non-narcotic analgesic such as acetylsalicylic acid, acetaminophen, ibuprofen, ketoprofen, and naproxen, or pharmaceutically acceptable salts thereof.

Additionally, the present invention includes a pharmaceutical composition for use in the treatment of cough, cold, cold-like and/or flu symptoms and the discomfort, pain, fever and general malaise associated therewith, in a human, said composition comprising (i) a therapeutically effective amount of at least one metabolic derivative of astemizole, with (ii) a therapeutically effective amount of a decongestant such as pseudoephedrine, or pharmaceutically acceptable salts thereof.

The present invention further encompasses a method for the treatment of cough, cold, cold-like, and/or flu symptoms and the discomfort, pain, fever, and general malaise associated therewith, in a human in need of such treatment, by administering to said human a composition comprising (i) a therapeutically effective amount of at least one metabolic derivative of astemizole, with (ii) a therapeutically effective amount of at least one non-steroidal anti-inflammatory agent or non-narcotic analgesic such as acetylsalicylic acid, acetaminophen, ibuprofen, ketoprofen, and naproxen, or pharmaceutically acceptable salts thereof.

Additionally, the present invention encompasses a method for the treatment of cough, cold, cold-like, and/or flu symptoms and the discomfort, pain, fever, and general malaise associated therewith, in a human in need of such is treatment comprising administering to said human a composition comprising (i) a therapeutically effective amount of at least one metabolic derivative of astemizole with (ii) a therapeutically effective amount of a decongestant such as pseudoephedrine, or pharmaceutically acceptable salts thereof.

A further aspect of this invention includes a method of treating an allergic reaction in a human with a composition comprising (i) a therapeutically effective amount of at least one metabolic derivative of astemizole, with (ii) a therapeutically effective amount of at least one non-steroidal anti-inflammatory agent or non-narcotic analgesic such as acetylsalicylic acid, acetaminophen, ibuprofen, ketoprofen, and naproxen, or pharmaceutically acceptable salts thereof.

Furthermore, the present invention includes a method of treating an allergic reaction in a human with a composition comprising (i) a therapeutically effective amount of at least one metabolic derivative of astemizole, with (ii) a therapeutically effective amount of a decongestant such as pseudoephedrine, or pharmaceutically acceptable salts thereof.

Astemizole has antihistaminic activity and provides therapy and a reduction of symptoms for a variety of conditions and disorders related to allergic disorders, diabetes mellitus and other conditions; however, this drug, while offering the expectation of efficacy, causes adverse effects. Utilizing the metabolic derivatives of astemizole results in clearer dose-related definitions of efficacy, diminished adverse effects, and accordingly, an improved therapeutic index. It is, therefore, more desirable to use metabolic derivatives of astemizole than to use astemizole itself, and the metabolic derivatives of astemizole may be administered in greater doses than would be appropriate for astemizole.

The term "adverse effects" includes, but is not limited to cardiac arrhythmias, cardiac conduction disturbances, appetite stimulation, weight gain, sedation, gastrointestinal distress, dry mouth, constipation, and diarrhea. The term "cardiac arrhythmias" includes, but is not limited to ventricular tachyarrhythmias, torsades de pointes, and ventricular fibrillation.

The phrase "therapeutically effective amount" means that amount of one or more of the metabolic derivatives of astemizole which provides a therapeutic benefit in the treatment or management of allergic disorders, asthma, retinopathy or other small vessel disorders associated with diabetes mellitus, motion sickness, vertigo, or cough, cold, cold-like, and/or flu symptoms and the discomfort, pain, fever, and general malaise associated therewith. Examples of allergic disorders include, but are not limited to, allergic rhinitis, solar urticaria, and symptomatic dermographism. The symptoms associated with these allergic disorders and the cough, cold, cold-like, and/or flu symptoms include, but are not limited to, sneezing, rhinorrhea, lacrimation, and dermal irritation. The term "asthma" is defined as a disorder characterized by increased responsiveness of the trachea and bronchi to various stimuli which results in symptoms which include wheezing, cough, and dyspnea. The term "vertigo" as used herein means the dizziness associated with, but not limited to, motion, height, and changes in body position. The term "diabetic retinopathy" or "retinopathy associated with diabetes mellitus" is that disorder caused by increased permeability of the capillaries in the eye which leads to hemorrhages and edema in the eye and can lead to blindness. The term "small vessel disorders associated with diabetes mellitus" includes, but is not limited to, diabetic retinopathy and peripheral vascular disease.

The magnitude of a prophylactic or therapeutic dose of the metabolic derivatives of astemizole in the acute or chronic management of disease will vary with the severity of the condition to be treated and the route of administration. The dose, and perhaps the dose frequency, will also vary according to the age, body weight, and response of the individual patient. In general, the total daily dose range, for the conditions described herein, is from about 1 mg to about 200 mg administered in single or divided doses orally, topically, transdermally, or locally by aerosol. For example, a preferred oral daily dose range is should be from about 1 mg to about 50 mg. It is further recommended that children, patients aged over 65 years, and those with impaired renal or hepatic function initially receive low doses, and that they then be titrated based on individual response(s) or blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response.

The various terms "an amount sufficient to alleviate said allergic disorder but insufficient to cause said adverse effects," "an amount sufficient to alleviate said asthma but insufficient to cause said adverse effects," "an amount sufficient to alleviate said motion sickness but insufficient to cause said adverse effects," and "an amount sufficient to alleviate said retinopathy or other small vessel diseases associated with diabetes mellitus but insufficient to cause said adverse effects" are encompassed by the above-described dosage amounts and dose frequency schedule. In addition, the terms "a pharmaceutical composition for use in the treatment of cough, cold, cold-like and/or flu symptoms and the discomfort, pain, fever and general malaise associated therewith, in a human, said composition comprising (i) a therapeutically effective amount of at least one metabolic derivative of astemizole, with (ii) a therapeutically effective amount of at least one non-steroidal anti-inflammatory agent or non-narcotic analgesic" and "a pharmaceutical composition for use in the treatment of cough, cold, cold-like and/or flu symptoms and the discomfort, pain, fever and general malaise associated therewith, in a human, said composition comprising (i) a therapeutically effective amount of at least one metabolic derivative of astemizole, with (ii) a therapeutically effective amount of a decongestant" are also encompassed by the above-described dosage amounts and dose frequency schedule.

Any suitable route of administration may be employed for providing the patient with an effective dosage of the metabolic derivatives of astemizole. For example, oral, rectal, parenteral, transdermal, subcutaneous, intramuscular, and like forms of administration may be employed. Dosage forms include tablets, troches, dispersions, suspensions, solutions, capsules, patches, and the like.

The pharmaceutical compositions of the present invention comprise the metabolic derivatives of astemizole as active ingredient, or a pharmaceutically acceptable salt thereof, and may also contain a pharmaceutically acceptable carrier, and optionally, other therapeutic ingredients.

The term "pharmaceutically acceptable salts" refers to salts prepared from pharmaceutically acceptable non-toxic acids or bases including inorganic acids or bases or organic acids or bases. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucoronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases include metallic salts made from aluminum, calcium, lithium, magnesium, potassium, sodium, and zinc. Appropriate organic bases may be selected, for example, from, N,N'-dibenzylethylenediamine, chloroprocaine, choline, diethanolamine, ethylenediamine, meglumaine (N-methylglucamine), lysine and procaine.

The compositions of the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more is accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet contains from about 5 mg to about 150 mg of the active ingredient, and each cachet or capsule contains from about 5 mg to about 150 mg of the active ingredient, i.e., a metabolic derivative of astemizole. Most preferably, the tablet, cachet or capsule contains either one of three dosages, 5 mg, 10 mg or 20 mg of the active ingredient.

The invention is further defined by reference to the following examples describing in detail the preparation of the compounds and the compositions of the present invention, as well as their utility. It will be apparent to those skilled in the art that many modifications, both to materials and methods, may be practiced which are within the scope of this invention.

4. EXAMPLES

4.1. Example 1

Preparation of Astemizole and its Metabolites

Atemizole can be synthesized by methods disclosed in U.S. Pat. No. 4,219,559. The metabolites are prepared similarly, by reaction steps conventional in the art, as depicted below:

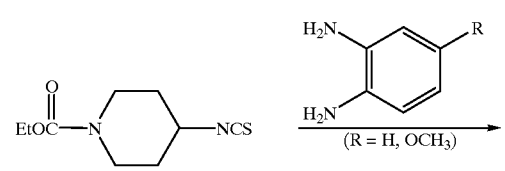

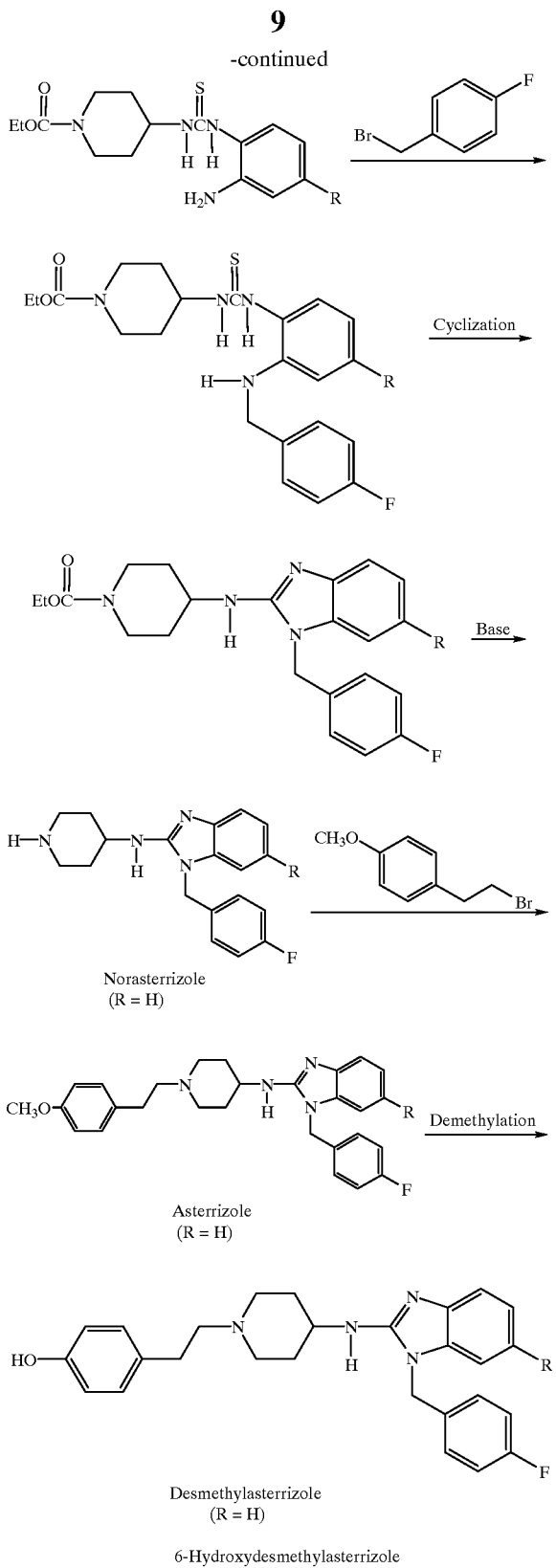

Norasterrizole (R = H)

Asterrizole (R = H)

Desmethylasterrizole (R = H)

6-Hydroxydesmethylasterrizole (R = OH)

Reaction of the isothiocyanate shown with phenylenediamine gives the corresponding thiourea. N-Alkylation with p-fluorobenzylbromide gives the secondary amine which, upon cyclization, yields the substituted benzimidazole shown. Treatment of the benzimidazole with base hydrolyzes the urethane moiety to give norastemizole. N-Alkylation of norastemizole with p-methoxyphenethyl bromide yields astemizole. Astemizole can be converted to desmethylastemizole by demethylation using, for example, a Lewis acid, such as boron trifluoride, boron trichloride, aluminum trichloride, and the like.

6-Hydroxydesmethylastemizole can be produced through a scheme analogous to that described above, using 3,4-diaminoanisole in place of phenylenediamine. The final deprotection step with Lewis acid can be made to cleave both aryl methyl ether moieties, yielding 6-hydroxydesmethylastemizole.

4.2. Example 2

Activities of astemizole and its metabolites at the histamine $H_1$-receptor are assessed using the [$^3$H]pyrilamine binding assay as described in Chang et al., *J. Neurochem.* 32: 1653–1663 (1979). Briefly, membranes from bovine cerebellum are incubated with [$^3$H]pyrilamine and varying concentrations of test compound. The reactions are carried out in 50 mM sodium phosphate buffer (pH 7.5) at 250° C. for 30 minutes. The reaction is terminated by rapid vacuum filtration onto glass fiber filters. Radioactivity trapped on the filters is determined and compared to control values to acertain the interaction of the test compound with the $H_1$-receptor.

4.3. Example 3

Single ventricular myocytes are obtained from isolated cat hearts by conventional techniques. The rod-shaped single cells are maintained in a HEPES buffer and then are "patch clamped" using suction pipettes. A Patch-Clamp L/M-PEC 7 amplifier is used to record current tracings and the recording electrodes are filled with a solution of potassium aspartate. Voltage clamp pulses and data acquisition are controlled by a Sperry PC/IT Computer running P Clamp software. A minimum of 4 cells are studied at each test concentration of the following drugs: astemizole, astemizole metabolites, and quinidine (as a reference compound).

4.4. Example 4

| Oral Formulation - Capsules: | | | |
|---|---|---|---|
| | Quantity per capsule in mg. | | |
| Formula | A | B | C |
| Active ingredient Astemizole metabolite | 5.0 | 10.0 | 20.0 |
| Starch 1500 | 69.0 | 39.0 | 9.0 |
| Magnesium Stearate BP | 1.0 | 1.0 | 1.0 |
| Compression Weight | 100.0 | 100.0 | 100.0 |

The active ingredient is sieved and blended with the excipients. The mixture is filled into suitably sized two-piece hard gelatin capsules using suitable machinery. Other doses may be prepared by altering the fill weight and if necessary, changing the capsule size to suit.

4.5. Example 5

Oral Formulation - Tablets:

| Formula | Quantity per Tablet in mg. | | |
|---|---|---|---|
| | A | B | C |
| Active ingredient, Astemizole metabolite | 5.0 | 10.0 | 20.0 |
| Lactose BP | 123.5 | 93.5 | 63.5 |
| Starch BP | 30.0 | 30.0 | 30.0 |
| Pregelatinized Maize Starch BP | 15.0 | 15.0 | 15.0 |
| Magnesium stearate | 1.5 | 1.5 | 1.5 |
| Compression Weight | 200.0 | 200.0 | 200.0 |

The active ingredient is sieved through a suitable sieve and blended with the lactose until a uniform blend is formed. Suitable volumes of water are added and the powders are granulated. After drying, the granules are then screened and blended with the magnesium stearate. The resulting granules are then compressed into tablets of desired shape. Tablets of other strengths may be prepared by altering the ratio of active ingredient to the excipient(s) or the compression weight.

What is claimed is:

1. A method for treating solar uticaria in a human which comprises administering to a human in need thereof a therapeutically effective amount of norastemizole, or a pharmaceutically acceptable salt thereof.

2. The method of claim 1, wherein the amount of norastemizole administered is from about 1 mg to about 200 mg per day.

3. The method of claim 1, wherein the amount of norastemizole administered is from about 1 mg to about 50 mg per day.

4. The method of claim 1, wherein the amount of norastemizole or pharmaceutical acceptable salt thereof is administered together with a pharmaceutically acceptable carrier.

5. A method for treating symptomatic dermographism in a human which comprises administering to a human in need thereof a therapeutically effective amount of norastemizole, or a pharmaceutically acceptable salt thereof.

6. The method of claim 5, wherein the amount of norastemizole administered is from about 1 mg to about 200 mg per day.

7. The method of claim 6, wherein the amount of norastemizole administered is from about 1 mg to about 50 mg per day.

8. The method of claim 5, wherein the amount of norastemizole or pharmaceutical acceptable salt thereof is administered together with a pharmaceutically acceptable carrier.

* * * * *